United States Patent [19]

Coupe

[11] 4,015,942

[45] Apr. 5, 1977

[54] APPARATUS FOR DELIVERING LIQUID AND REMOVING LIQUID FROM A CONTAINER

[75] Inventor: Neville Burton Coupe, Billingshurst, England

[73] Assignee: Denley-Tech Limited, Sussex, England

[22] Filed: Dec. 5, 1975

[21] Appl. No.: 638,099

[30] Foreign Application Priority Data

Dec. 10, 1974 United Kingdom ............ 53431/74

[52] U.S. Cl. .............................. 23/259; 141/279; 195/139; 251/9

[51] Int. Cl.² ................... B01L 11/00; B67C 3/28; F16L 55/14

[58] Field of Search ......... 23/259, 253 R; 195/127, 195/139, 142; 417/475; 141/279; 251/9

[56] References Cited

UNITED STATES PATENTS

| | | | |
|---|---|---|---|
| 3,081,158 | 3/1963 | Winter | 23/253 R |
| 3,098,719 | 7/1963 | Skeggs | 23/253 R |
| 3,098,819 | 7/1963 | Sager | 23/253 R X |
| 3,572,994 | 3/1971 | Hochstrasser | 23/253 R X |
| 3,684,452 | 8/1972 | Bessman | 23/259 X |
| 3,723,030 | 3/1973 | Gelfand | 417/475 |
| 3,801,283 | 4/1974 | Shapiro et al. | 23/259 X |
| 3,875,000 | 4/1975 | Kaneda | 195/127 X |

Primary Examiner—Joseph Scovronek

[57] ABSTRACT

The invention relates to a new apparatus for delivering liquid to a plurality of containers and removing contents therefrom comprising a plurality of pairs of tubes each tube having or being connected to a constrictible tube portion. A first tube of each pair is adapted to deliver liquid to a respective container from a liquid supply and the second tube of each pair is adapted for connection between suction means and a tube portion adapted to project into a respective container to remove liquid therefrom. Tube constricting means are provided and arranged to constrict said tube portions alternately whereby respectively liquid is delivered to each container and contents removed therefrom.

10 Claims, 1 Drawing Figure

U.S. Patent  April 5, 1977  4,015,942
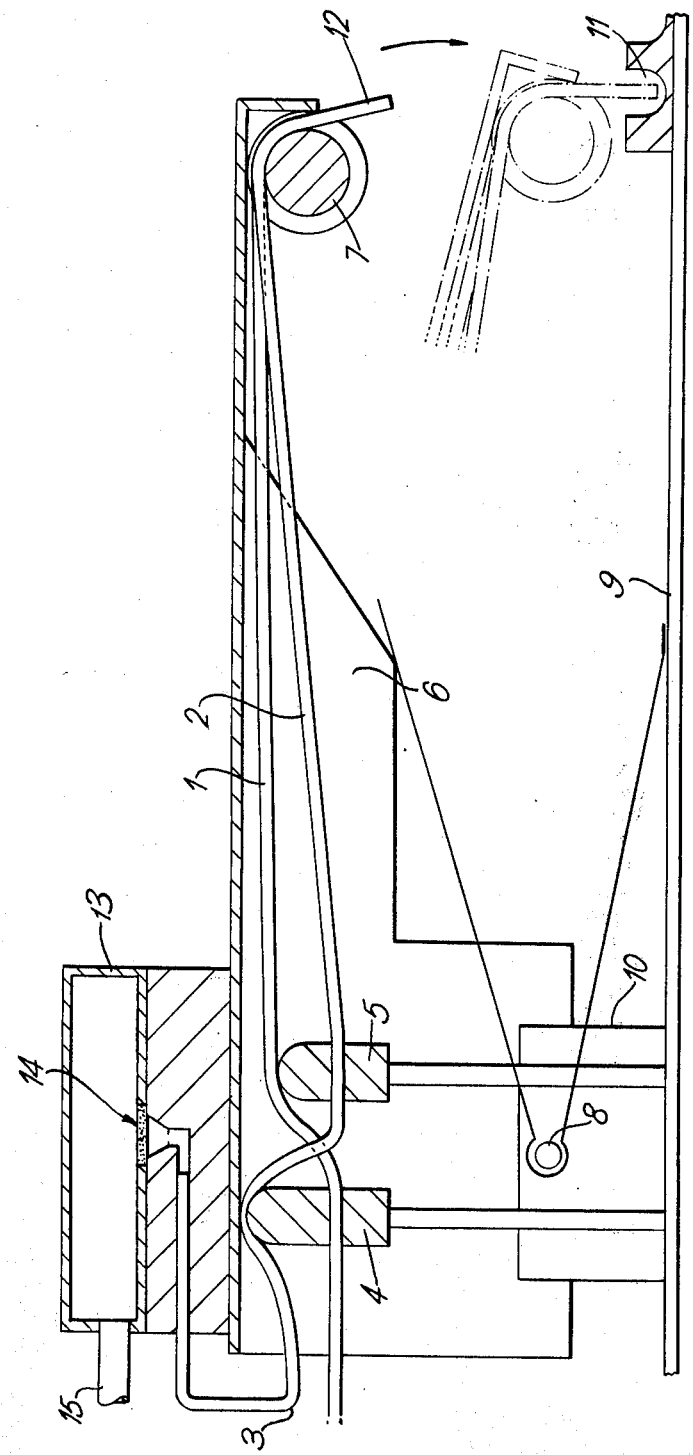

APPARATUS FOR DELIVERING LIQUID AND REMOVING LIQUID FROM A CONTAINER

The present invention relates to apparatus for delivering liquid to and removing the contents from a plurality of containers. The apparatus of the present invention is particularly, but not exclusively, applicable to the delivery of liquid to and the removal of the contents from wells in a plate, which wells are employed for tissue culture work or, for example, for serological and bacteriological testing procedures.

Apparatus for the above-mentioned purposes hitherto marketed have tended to be expensive and to involve electronic components such that use of the apparatus is highly automated. There is a need for effective relatively inexpensive apparatus which would be capable of delivering liquid to and removing the contents from, for example, wells in microbiological testing plates.

The present invention is based upon the discovery that effective and relatively inexpensive apparatus may be produced employing squeeze valves, i.e. valves in which flow may, if desired, be prevented by squeezing or constricting a constrictible tube or pipe.

Thus, according to the invention there is provided apparatus for delivering liquid to a plurality of containers and for removing contents therefrom comprising a plurality of pairs of tubes each tube having or being connected to a constrictible tube portion, a first tube of each pair being adapted to deliver liquid to a respective container from a liquid supply, the second tube of each pair being adapted for connection between suction means and a tube portion adapted to project into a respective container to remove liquid therefrom, and tube constricting means arranged to automatically constrict said tube portions alternately and in dependence upon the position of the tubes relative to the containers whereby respectively to deliver liquid to each container and remove contents therefrom.

Although if desired all of said first tubes and second tubes could be connected to a respective single constrictible tube portion, it is preferred that each tube is constrictible along at least part of its length and said constricting means is arranged to constrict said first and second tubes of each pair. Indeed it is generally preferable that the second tubes are not joined but are separate and constrictible so that the contents being removed from each of the plurality of containers may be kept separated and filtered or otherwise examined if necessary.

Preferably, said tubes are mounted in or on a pivotable member and said tube constricting means comprises abutment means adapted to effect said alternate constriction on pivoting of said member between first and second positions, in which case said pivotable member may comprise a housing for the said tubes.

The apparatus is conveniently provided with a means for effecting master control of the liquid supply and this may take the form of, for example, a handle or switch which might, for example, be arranged to control a squeeze valve comprising a constrictible supply tube, or a simple on/off valve e.g. a tap.

The apparatus of the present invention may also, if desired, comprise respective third tubes connected to suction means e.g. a vacuum pump for removing any excess of liquid delivered to the containers in error via the first tubes. The suction in the third tube is, in general, continually maintained throughout operation of the apparatus of the invention. Unlike the first and second tubes, the third tubes are not, in general, subject to any constrictive control, but are continuously operational during operation of the apparatus.

In one embodiment of the present invention the second tubes are longer than the first tubes so that the second tubes are capable, in the second position, of extending to the bottom of the containers from which it is desired to remove the contents; the first tubes may merely serve to deliver liquid to the container and may therefore be shorter in length than the second tubes.

The apparatus of the present invention is, in one embodiment, combined with a filter system e.g. a filter bed. Thus, the second tubes are connected to the filter system so that in the second position of the apparatus of the present invention the contents of the container are removed by suction and pass through the second tubes to the filter system where the contents of the containers are conveniently suction filtered.

The apparatus of the present invention is of particular interest and application in microbiology e.g. bacteriology, immunohaematology, mycology, parasitology, serology, virology and V.D. serology. In this connection plates containing many wells e.g. 'Microtiter' (Registered Trade Mark) plates are used, various cultures and test procedures being carried out in the wells. Thus the plates may be used for various microbiological purposes and the apparatus of the present invention may be employed for series dilution to wash out the contents of each of the wells and transfer these substances to a filter system. The apparatus of the present invention may thus, for example, be used as an aid in the rapid assay of mixed lymphocyte cultures (e.g. histocompatibility studies), drug sensitivity testing, determination of reactivity of tumour cells to substances and determination of in vitro lymphocyte responsiveness. The apparatus may also be used for determining the cellular uptake of labelled compounds.

In one embodiment of the present invention the apparatus comprises 12 pairs of first and second tubes thus enabling, for example, 12 wells in a microbiological culture plate to be washed out simultaneously and their contents removed for filtration.

In one embodiment of the present invention the apparatus is mounted on a base plate which can support, for example, the 'Microtiter' (Registered Trade Mark) plate. The tubes for delivery of liquid to the wells in the plate and for removal of the contents of the wells are mounted in a pivotable member. The pivotal member may take the form of a limb which is pivotally attached at one end to a holding member which in turn is attached to the base plate. The other end of the limb extends out over the base plate such that each first tube is capable of being positioned over each of the wells of the microbiological culture plate. The limb is biased to remain in a position substantially parallel to the base plate, in which position liquid is delivered to the wells of the microbiological test plate via the first tubes while the suction at the free ends of the second tubes is shut off by constriction. Depression of the limb i.e. towards the base plate causes constriction of the first tubes and thus shuts off the liquid supply and opens the second tubes to allow the contents to be removed by suction.

The tubes must consist, at least in part, of a constrictible material e.g. silicone rubber, but may additionally consist of rigid tubing e.g. of stainless steel.

The invention will best be understood from the following description of an exemplary embodiment thereof with reference to the accompanying drawing which shows a cross-section through an apparatus of the present invention having 12 pairs of tubes, the cross-section only showing one such pair of tubes, the first tube of each pair being open to allow liquid to be delivered to a well.

The drawing depicts a first tube 1 through which liquid is delivered from the liquid supply (not shown) to the well. A tap (not shown) is provided to effect master control of the liquid supply through each first tube. A second tube 2 is connected at end 3 to a vacuum pump via a filter system 13. The filter system 13 consists of a block extending above and below the plane of the paper and comprising a filter bed of 12 filter wells, the filter element of one of the filter wells being depicted in the drawing at 14. Both tube 1 and tube 2 pass over constricting bars 5 and 4 respectively and the tubes are held in position against the pivotable support member 6 of an elongated arm by holding means 7. The constricting bars 4 and 5 consist of two bars extending above and below the plane of the paper and are thus adapted to respectively effect constriction of each second tube of the 12 pairs of tubes simultaneously and each first tube of the 12 pairs of tubes simultaneously. The holding means 7 consists of a cylinder extending above and below the plane of the paper, the diameter of the cylinder being alternately reduced and increased to allow passage of each pair of tubes around the portion of reduced diameter while each pair of tubes is separated and retained against substantial lateral movement by the portion of increased diameter. The pivotable member 6 is rotated about pivot pin 8 mounted on a support member 10 which is affixed to the base plate 9. The pivotal arm support member 6 and is spring biased into its first or uppermost position by a lock spring the apex of which is positioned around the pivot pin 8. One arm of the lock spring acts against the base plate 9 while the other arm of the lock spring acts against the pivotable arm support member 6 as shown.

The operation liquid is delivered to the well 11 via tube 1. When well 11 has been filled the pivotable member 6 is depressed such that the free end 12 of suction tube 2 projects into the base of the well 11 as shown in the fragmentary detail. Depression of the pivotable member 6 causes the tube 1 to be constricted between the constricting bar 5 and the pivotable member 6 thus shutting off the supply of liquid. Simultaneously the pivotable member 6 is raised off the constricting bar 4 thus allowing the contents of the well to be removed from the well 11 via the tube 2 by suction. The contents of the well 11 thus pass into the filter system 13, the solids being retained by the filter disc 14. The discharge conduits 15 from the filter system 13 is connected to a vacuum pump (not shown).

It will be appreciated that other modifications may be made to the above described invention without departing from the scope of the invention.

I claim:

1. Apparatus for use in the delivery of liquid to and the withdrawal of material from containers comprising:
   at least a first pair of conduit means, said conduit means of said pair of each including a constrictible tubular portion, a first of said conduit means of said pair having a free end for delivery of liquid to a container and the second of said conduit means having a free end for withdrawal of material from the container by suction;
   pivotable support means for said conduit means, said support means mounting said conduit means such that the free ends thereof may be simultaneously moved relative to the container between a first position and a second position;
   first abutment means, said first abutment means being fixedly mounted relative to said support means for compressing said second conduit means constrictible portion when said support means is in the first position whereby material may not be withdrawn through said second conduit means when said pivotable support means is in the first position; and
   second abutment means, said second abutment means being fixedly mounted relative to said support means for compressing said first conduit means constrictible portion when said support means is in the second position whereby liquid may not be supplied through said first conduit means when said pivotable support means is in the second position.

2. The apparatus of claim 1 wherein said conduit means of each pair each comprises:
   an elongated tube, said tube being constrictible along at least a portion of its length.

3. The apparatus of claim 2 wherein said support means comprises:
   elongated arm means;
   means for holding said tubes on said arm means with the free ends thereof adjacent a first end of said arm means; and
   means for pivotally supporting said arm means adjacent the second end thereof.

4. The apparatus of claim 1 further comprising:
   means for spring biasing said pivotable support means to said first position.

5. The apparatus of claim 3 further comprising:
   means for spring biasing said elongated arm means to said first position.

6. The apparatus of claim 1 wherein said abutment means each comprises:
   a bar positioned so as to compress said conduit means constrictible tubular portion against said pivotable support means.

7. The apparatus of claim 3 wherein said abutment means each comprises:
   a bar positioned so as to compress said tube constrictible portion against said elongated arm means.

8. The apparatus of claim 7 further comprising:
   means for spring biasing said elongated arm means to said first position.

9. The apparatus of claim 1 further comprising:
   filter means for separating particulate matter from material withdrawn from a container through said second conduit means, said filter means being mounted on said support means so as to be in serial fluid communication with said second conduit means.

10. The apparatus of claim 9 further comprising:
    filter means for separating particulate matter from material withdrawn from the container through said second conduit means, said filter means being mounted on said arm means and being in serial fluid communication with the second end of said second conduit means elongated tube.

* * * * *

UNITED STATES PATENT AND TRADEMARK OFFICE
CERTIFICATE OF CORRECTION

PATENT NO. : 4,015,942
DATED : April 5, 1977
INVENTOR(S) : Neville B. Coupe

It is certified that error appears in the above-identified patent and that said Letters Patent are hereby corrected as shown below:

Column 3, line 37, after "6" delete --and--

Column 3, line 43, "The" should be --In--

Column 3, line 56, "conduits" should be --conduit--

Column 4, line 61, (Claim 10, line 1), "9" should be --8--

Signed and Sealed this twelfth Day of July 1977

[SEAL]

Attest:

RUTH C. MASON
*Attesting Officer*

C. MARSHALL DANN
*Commissioner of Patents and Trademarks*